(12) United States Patent
Wu et al.

(10) Patent No.: US 12,109,317 B2
(45) Date of Patent: Oct. 8, 2024

(54) ELECTROSPUN FIBROUS MATRIX, ITS PREPARATION METHOD AND USES THEREOF

(71) Applicant: NATIONAL CHENG KUNG UNIVERSITY, Tainan (TW)

(72) Inventors: Ping-Ching Wu, Tainan (TW); Cheng-Hsin Chuang, Tainan (TW); Po-Heng Chen, Taoyuan (TW); Yu-Yi Chiang, Taichung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 132 days.

(21) Appl. No.: 17/564,096

(22) Filed: Dec. 28, 2021

(65) Prior Publication Data

US 2023/0201129 A1    Jun. 29, 2023

(51) Int. Cl.

| | | |
|---|---|---|
| *A61K 9/70* | (2006.01) | |
| *A61K 9/16* | (2006.01) | |
| *A61K 31/573* | (2006.01) | |
| *A61K 35/15* | (2015.01) | |
| *A61K 35/33* | (2015.01) | |
| *A61K 47/32* | (2006.01) | |
| *A61K 47/34* | (2017.01) | |
| *A61L 15/26* | (2006.01) | |
| *A61L 15/44* | (2006.01) | |
| *A61L 27/38* | (2006.01) | |
| *A61L 27/56* | (2006.01) | |
| *C08L 29/04* | (2006.01) | |
| *C08L 67/04* | (2006.01) | |
| *D01D 5/00* | (2006.01) | |
| *D01F 1/10* | (2006.01) | |
| *A61P 17/02* | (2006.01) | |

(52) U.S. Cl.
CPC .............. *A61K 9/70* (2013.01); *A61K 31/573* (2013.01); *A61K 35/15* (2013.01); *A61K 35/33* (2013.01); *A61K 47/32* (2013.01); *A61K 47/34* (2013.01); *A61L 15/26* (2013.01); *A61L 15/44* (2013.01); *C08L 29/04* (2013.01); *C08L 67/04* (2013.01); *D01D 5/0015* (2013.01); *D01F 1/10* (2013.01); *A61P 17/02* (2018.01); *C08L 2203/02* (2013.01); *C08L 2203/12* (2013.01)

(58) Field of Classification Search
CPC ........ A61K 9/70; A61K 31/573; A61K 35/15; A61K 35/33; A61K 47/32; A61K 47/34; A61K 9/1647; A61L 15/26; A61L 15/44; A61L 27/18; A61L 27/54; C08L 29/04; C08L 67/04; C08L 2203/12; A61P 17/02; C08G 63/06; C08K 9/10; D01F 8/16; D01D 5/0007

See application file for complete search history.

(56) References Cited

U.S. PATENT DOCUMENTS

2009/0196901 A1*  8/2009  Guilak ................. C12N 5/0667
                                                                435/6.16
2020/0038327 A1*  2/2020  Mallery ............... A61K 31/167

OTHER PUBLICATIONS

Padmakumar et al., Long-term drug delivery using implantable electrospun woven polymeric nanotextiles, Nanomedicine: Nanotechnology, Biology and Medicine, vol. 15, Issue 1, pp. 274-284. (Year: 2019).*

Whitehead, T.J., Sundararaghavan, H.G. Electrospinning Growth Factor Releasing Microspheres into Fibrous Scaffolds. J. Vis. Exp. (90), e51517, pp. 1-9. (Year: 2014).*

* cited by examiner

*Primary Examiner* — Abigail Vanhorn

(74) *Attorney, Agent, or Firm* — NZ CARR LAW OFFICE

(57) ABSTRACT

Disclosed herein are electrospun fibrous matrix and its production method. The method mainly includes the steps of, mixing a first polymer and a drug to form a first mixture, and sonicating the first mixture until a plurality of microparticles are formed with the drug encapsulated therein; and mixing the plurality of microparticles with a second polymer to form a second mixture, subjecting the second mixture to a wet electrospinning process to form the electrospun fibrous matrix. The thus-produced electrospun fibrous matrix is characterized by having a plurality of first and second fibrils woven together, in which each second fibril has a plurality of drug-encapsulated microparticles independently integrated and disposed along the longitudinal direction of the second fibril. Also disclosed herein is a method for treating a wound of a subject. The method includes applying the present electrospun fibrous matrix to the wound of the subject.

15 Claims, 9 Drawing Sheets

ELECTROSPUN FIBROUS MATRIX, ITS PREPARATION METHOD AND USES THEREOF

BACKGROUND OF THE INVENTION

1. Field of the Invention

The present disclosure relates to an electrospun fibrous matrix. More particularly, the disclosure invention relates to the electrospun fibrous matrix suitable for use as a biocompatible scaffold for cells to grow thereon, thus the electrospun fibrous matrix are useful as implants for the treatment of wounds.

2. Description of Related Art

A wound is an injury involving an external or internal break in body tissue. Wounds are often caused by chemical agents, burns, physical trauma, neuropathic ulcers, pressure sores, venous stasis ulcers, and/or diabetic ulcers, and in most cases accompanied by infection and inflammation. When the injured lesion occurs on the dental pulp of one subject, it becomes pulpitis.

Normal wound healing is an enormously complex process involving the coordinated interplay between fibroblasts, vascular cells, extracellular matrix and epithelial cells to result in a seamless progression through an inflammatory reaction, wound repair, contracture and coverage by an epithelial barrier. A bio-scaffold is optionally or additionally required for restoring specific tissues; for example, an acellular collagen scaffold implanted into the lesions can help skin repair or a cartilage reconstruction.

However, in many patients, due to either the local wound environment or systemic diseases, the wound healing processes may become asynchronous (i.e., loss of connectivity with triggering mechanisms associated with prior cellular events) and are unable to progress to closure. Though a biodegradable substance might help to encourage the cells to repair itself, cell seeding density and cell attachment ratio are limited by various materials and structures, resulting a low efficiency of tissue regeneration. Moreover, the medication might not be able to penetrate the deep lesion of the wound, which slows down the wound healing processes.

In view of the foregoing, there exists in the related art a need of an improved biocompatible matrix with drug-delivery function for treatment to any injuries or wounds described above, particularly the lesion on the dental pulp.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the present disclosure is directed to an electrospun fibrous matrix comprising a plurality of a first and second fibrils that are woven together, wherein each of the second fibrils has a plurality of microparticles independently integrated and disposed along the longitudinal direction of the second fibrils, while each of the first fibrils is devoid of the microparticles integrated therein; each of the microparticles is made of a first polymer and has a drug encapsulated therein; and the plurality of the first and second fibrils are independently made of a second polymer that is different from the first polymer.

According to some embodiments of the present disclosure, each of the first fibrils has a diameter ranging from 100 to 500 nm, and each of the microparticles is about 1 to 5 μm in diameter.

According to some embodiments of the present disclosure, the electrospun fibrous matrix has a plurality of cavities independently being about 15-40 μm in diameter.

According to some embodiments of the present disclosure, the first polymer and the second polymer are respectively selected from the group consisting of polyurethanes, polysiloxanes, polyethylene, poly(vinyl pyrrolidone), poly (2-hydroxyethyl methacrylate), poly(methyl methacrylate), poly(vinyl alcohol) (PVA), polyacrylic acid, polyacrylamide, poly(ethylene-co-vinyl acetate), poly(ethylene glycol), poly(methacrylic acid), polylactic acid (PLA), polyglycolic acids (PGA), poly(lactic-co-glycolic acid) (PLGA), nylons, polyamides, polyanhydrides, poly(ethylene-co-vinyl alcohol) (EVOH), polycaprolactone (PCL), poly(vinyl acetate), poly(vinyl hydroxide), poly(ethylene oxide) (PEO) and polyorthoesters.

In some preferred embodiments, the first polymer is PLGA, and the second polymer is PVA.

According to some embodiments of the present disclosure, the drug is an analgesic agent, an anti-inflammatory agent, an anti-cancer agent, an antibiotic, or a combination thereof.

Another aspect of the present disclosure is directed to a method of producing an electrospun fibrous matrix. The method comprises: (a) mixing a first polymer and a drug to from a first mixture; (b) sonicating the first mixture of the step (a) until a plurality of microparticles are formed with the drug being encapsulated therein; (c) mixing the plurality of microparticles of the step (b) with a second polymer to form a second mixture; (d) subjecting the second mixture of the step (c) to an electrospinning process in a solution to produce a plurality of first and second fibrils, wherein each of the second fibrils has the plurality of microparticles independently integrated and disposed along the longitudinal direction of the second fibrils, while each of the first fibrils is devoid of the microparticles; and (e) weaving the plurality of first and second fibrils to form the electrospun fibrous matrix, wherein the first polymer and the second polymer are different.

According to some embodiments of the present disclosure, in the step (a) of the method, the first polymer and the drug are mixed at a mass ratio about 5:1 to 3:1.

According to some embodiments of the present disclosure, the first polymer and the second polymer exist in a mass ratio of about 1:5 to 1:15.

In some embodiments of the present disclosure, the first polymer and the second polymer are respectively selected from the group consisting of polyurethanes, polysiloxanes, polyethylene, poly(vinyl pyrrolidone), poly(2-hydroxyethyl methacrylate), poly(methyl methacrylate), poly(vinyl alcohol) (PVA), polyacrylic acid, polyacrylamide, poly(ethylene-co-vinyl acetate), poly(ethylene glycol), poly(methacrylic acid), polylactic acid (PLA), polyglycolic acids (PGA), poly(lactic-co-glycolic acid) (PLGA), nylons, polyamides, polyanhydrides, poly(ethylene-co-vinyl alcohol) (EVOH), polycaprolactone (PCL), poly(vinyl acetate), poly(vinyl hydroxide), poly(ethylene oxide) (PEO) and polyorthoesters.

In some preferred embodiments, the first polymer is PLGA, and the second polymer is PVA.

According to some embodiments of the present disclosure, the drug is an analgesic agent, an anti-inflammatory agent, an anti-cancer agent, an antibiotic, or a combination thereof.

According to some embodiments of the present disclosure, in the step (d), the electrospinning process is conducted under a humidity of about 20-55% at a voltage of about 16-22 kV for about 5 hours.

In some embodiments of the present disclosure, in the step (d), the solution is a methanol solution.

Still another aspect of the present disclosure is directed to a method for treating a wound in a subject in need thereof, comprising applying the abovementioned electrospun fibrous matrix or the electrospun fibrous matrix produced by the method stated above to the wound of the subject.

Optionally, the treating method further comprises administering to the subject an effective amount of isolated stem cells, isolated somatic cells, or a combination thereof.

Examples of the stem cells include, but are not limited to, mesenchymal stem cells, adult stem cells, embryonic stem cells, bone marrow stem cells, neural stem cells, limbal stem cells, tissue-derived stem cells, dental pulp stem cells, and induced pluripotent stem cells.

Examples of the somatic cells include, but are not limited to, muscle cells, hepatocytes, neurons, fibroblasts, odontoblasts, epithelial cells, adipocytes, bone cells, leukocytes, lymphocytes, platelets, and mucosal cells.

According to some embodiments of the present disclosure, the isolated stem cells or the isolated somatic cells are administered to the subject in the amount of about $1\times10^4$ to $1\times10^6$ cells per square centimeter of a wound area.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1A:
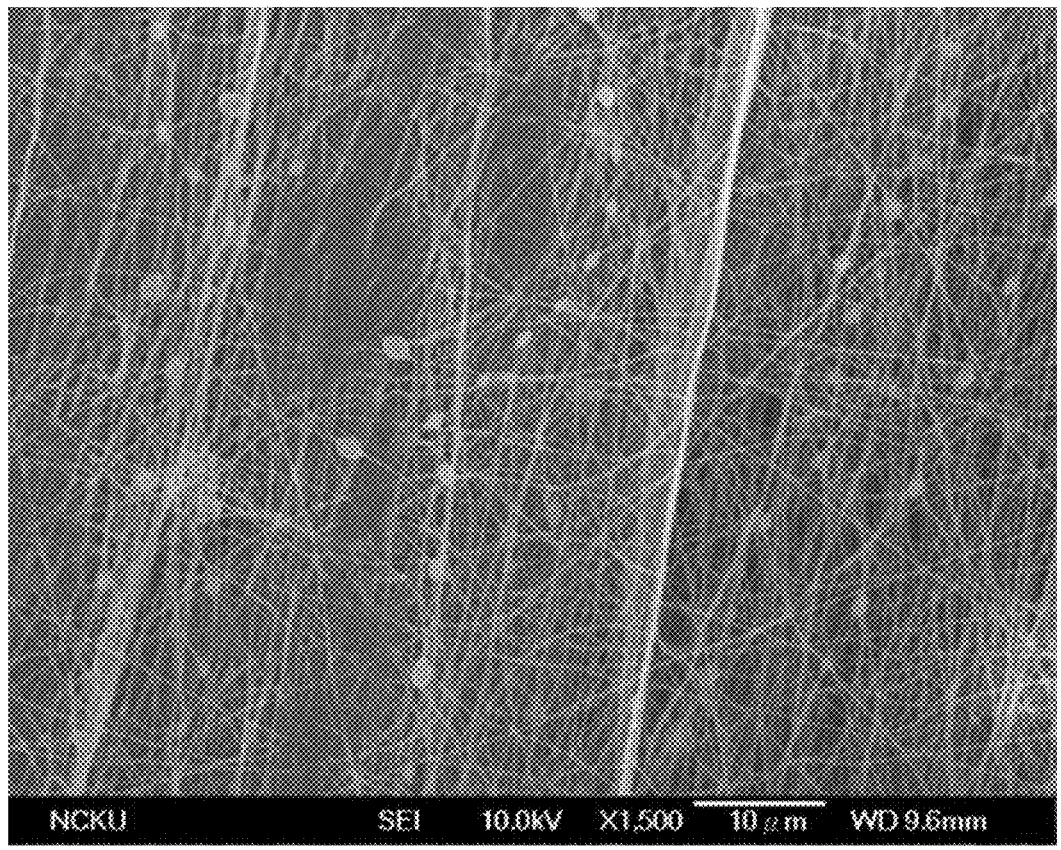
FIGS. 1A and 1B are electron microscopic photos respectively depicting the structure of an electrospun fibrous matrix under different magnification, according to one embodiment of the present disclosure, magnification: 1500× in FIG. 1A, and 9000× in FIG. 1B.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

The term "treatment" as used herein are intended to mean obtaining a desired pharmacological and/or physiologic effect, e.g., reducing the pain and accelerating the healing processes of a wound. The effect may be prophylactic in terms of completely or partially preventing a symptom thereof and/or therapeutic in terms of a partial or complete cure for a disease and/or adverse effect attributable to the disease. "Treatment" as used herein includes curative or palliative treatment of a disease in a mammal, particularly human; and includes: (1) inhibiting a condition (e.g., by arresting a wound's development in dental pulp); or (2) relieving a condition (e.g., reducing inflammation and pains associated with the wound).

The term "administered", "administering" or "administration" are used interchangeably herein to refer a mode of delivery, including, without limitation, intravenously, intramuscularly, intraperitoneally, intraarterially, intracranially, or subcutaneously administering isolated cells (e.g., isolated stem cells and/or isolated somatic cells) that improve the wound healing.

The term "an effective amount" as used herein refers to an amount effective, at dosages, and for periods of time necessary, to achieve the desired result with respect to the treatment of a wound. For example, in the treatment of a wound, isolated cells (i.e., the present dental pulp stem cells) is administered in an amount that effectively attach to and grown on the electrospun fibrous matrix to treat the wound. An effective amount of an agent (e.g., isolated cells) is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total number of the isolated cells to body mass (e.g., kilograms) or total weight (e.g., mg) of an agent to the body mass (i.e., mg/kg). The effective amount may be divided into one, two or more doses in a suitable form to be administered at one, two or more times throughout a designated time period.

The term "subject" or "patient" is used interchangeably herein and is intended to mean a mammal including the human species that is treatable by the electrospun fibrous matrix of the present invention. The term "mammal" refers to all members of the class Mammalia, including humans, primates (e.g., monkey, and chimpanzee), domestic and farm animals, such as rabbit, pig, goat, sheep, and cattle; as well as zoo, sports or pet animals (e.g., a horse, a dog, a cat and etc); and rodents, such as mouse, rat, guinea pig, and hamster. In a working example, the subject is a human. Further, the term "subject" or "patient" intended to refer to both the male and female gender unless one gender is specifically indicated.

2. Detail Description of Preferred Embodiments

The present disclosure is based, at least in part, on the development of an electrospun fibrous matrix that is woven by a first and a second fibrils, wherein the second fibrils independently have a plurality of drug-containing microparticles which provide sustained drug release thereby improving the therapeutic efficacy of the drug. Accordingly, the present disclosure provides a novel fibrous matrix that serves as a bio-scaffold for wound healing and tissue regeneration. Also disclosed herein is production method of the present electrospun fibrous matrix.

2.1 Electrospun Fibrous Matrix and its Preparation Methods

The present disclosure aims at providing an electrospun fibrous matrix formed by weaving two types of fibrils, in which one type of fibrils are independently integrated with multiple drug-containing microparticles, while the other type of fibrils are not. According to embodiments of the present disclosure, the present electrospun fibrous matrix is produced by,
(a) mixing a first polymer and a drug to form a first mixture;
(b) sonicating the first mixture of the step (a) until a plurality of microparticles are formed with the drug being encapsulated therein;
(c) mixing the plurality of microparticles of the step (b) with a second polymer to form a second mixture;
(d) subjecting the second mixture of the step (c) to an electrospinning process in a solution to produce a plurality of first and second fibrils, wherein each of the second fibrils has the plurality of microparticles independently integrated and disposed along the longitudinal direction of the second fibrils, while each of the first fibrils is devoid of the microparticles; and
(e) weaving the plurality of first and second fibrils to form the electrospun fibrous matrix.

The present electrospun fibrous matrix is characterized in having drug-encapsulated microparticles in the electrospun fibrils, which are woven into a fibrous matrix suitable for supporting cells to grow therein. For the purpose of forming drug encapsulating microparticles, the drug is mixed together with a first polymer to form a first mixture, which is subsequently subjected to a sonication treatment, so that a plurality of microparticles are formed with the drug being encapsulated therein as drug-delivery vesicles. According to some embodiments of the present disclosure, the first polymer and the drug are independently dissolved in solvents and then mixed to produce a liquid mixture (steps (a) and (b)). In some embodiments, the first polymer and the drug are mixed at a mass ratio about 5:1 to 3:1, such as 5:1, 4:1, and 3:1. In one working example, the first polymer and the drug has a mass ratio of about 4:1.

According to embodiments of the present disclosure, the drug is capable of treating, reducing the risk for, or delaying the onset of wounds as described herein. Examples of the drug suitable for use in the present disclosure include, but are not limited to, an analgesic agent, an anti-inflammatory agent, an anti-cancer agent, an antibiotic, and a combination thereof that is encapsulated into the microparticles can be applied to the lesion of any subject in need. The exemplary analgesic agent suitable for use in the present disclosure for treating wounds includes, but is not limited to, paracetamol, nefopam, codeine, amitriptyline, gabapentin, morphine, oxycodone, pregabalin, tapentadol, hyoscine butylbromide, and tramadol. Examples of anti-inflammatory agent suitable for use in the present disclosure for treating wounds include, but are not limited to, acetylsalicylic acid, celecoxib, diclofenac diflunisal, etodolac, ibuprofen, indomethacin, ketoprofen, ketorolac, meloxicam, nabumetone, naproxen, oxaprozin, piroxicam, salsalate, sulindac, tolmetin, cortisone, methylprednisolone, betamethasone, prednisone, prednisolone, triamcinolone, dexamethasone, hydrocortisone, and fludrocortisone. Examples of anti-cancer agent suitable for use in the present electrospun fibrous matrix and/or the present methods include, but are not limited to, cisplatin, gemcitabine, doxorubicin, docetaxel, paclitaxel, carfilzomib, nobiletin, tangeretin, and a combination thereof. Examples of antibiotics suitable for use in the present disclosure include, but are not limited to, amoxicillin, penicillin, benzathine benzylpenicillin, cephalosporin and its derivatives (e.g., cefadroxil, cephalexin, cefaloglycin, cefalonium, and the like), clindamycin, macrolide and its derivatives (e.g., azithromycin, clarithromycin, fidaxomicin, and the like), chloramphenicol, erythromycin, spectinomycin, and a combination thereof. In one working example, the drug encapsulated in the microparticle is dexamethasone; in another working example, the drug encapsulated in the microparticles is celecoxib. In some optional or additional working examples, the drug is paclitaxel, nobiletin, or tangeretin.

Then, the plurality of drug encapsulating microparticles as described above are mixed with a second polymer. In general, this step aims to stabilize the particles and to have them relatively similar in sizes. The mixing may be conducted by any means known to those skilled persons in the art. In general, the mixture containing the drug encapsulating microparticles is stirred under a low vacuum condition. According to some embodiments of the present application, the first mixture is stirred with the aid of a magnetic stirrer at 30-50° C. under a low vacuum condition, which is to remove solvents present in the liquid mixture, for at least 10 minutes. Then, the first mixture is centrifuged to collect the microparticles for subsequent spinning process.

Once the plurality of microparticles are collected, the second polymer is added therein to form a second mixture, which exists as another liquid mixture (the step (c). After fully mixed, the second mixture is subjected to an electrospinning process in a solution to produce the first and the second fibrils (step (d)), in which the first fibrils differ from the second fibrils in that they are devoid of the drug encapsulating microparticles. The electrospinning process may be conducted by any means known to those skilled persons in the art. In general, the electrospinning is driven by a high voltage ranging from 10 to 30 kV, which is applied to the droplets of the second mixture at a flow rate of about 0.5 to 1.2 mL/hour, for a period of about 1 to 10 hours, thereby creating a polymeric jet that was shot into a solution, in which the first and second fibrils are respectively formed. The humidity of the surrounding environment may be in the range of about 10-60%. In one working example, the electrospinning is conducted at a humidity of about 20-55% at the voltage of about 16-22 kV for about 5 hours in methanol.

Two types of fibrils, the fibrils with or without integrated drug containing microparticles, are produced by the electrospinning described above. In the present disclosure, "the first fibril(s)" refers to the spun fibrils that are devoid of any drug containing microparticles; and "the second fibril(s)" refers to the spun fibrils independently having the plurality of drug-encapsulating microparticles disposed thereon along its longitudinal direction.

According to embodiments of the present disclosure, each of the first fibrils has a diameter ranging from 100 to 500 nm, such as 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nm; more preferably, each first fibril has a diameter ranging from 200 to 300 nm, such as 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, or 300 nm. On the other hand, each of the microparticles has a diameter ranging from 1 to 5 μm, such as 1, 1.5, 2, 2.5, 3, 3.5, 4, 4.5, or 5 μm; more preferably, each microparticle has a diameter ranging from 1.5 to 3.5 μm, such as 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, 2, 2.01, 2.02, 2.03, 2.04, 2.05, 2.06, 2.07, 2.08, 2.09, 2.1, 2.11, 2.12, 2.13, 2.14, 2.15, 2.16, 2.17, 2.18, 2.19, 2.2, 2.21, 2.22, 2.23, 2.24, 2.25, 2.26, 2.27, 2.28, 2.29, 2.3, 2.31, 2.32, 2.33, 2.34, 2.35, 2.36, 2.37, 2.38, 2.39, 2.4, 2.41, 2.42, 2.43, 2.44, 2.45, 2.46, 2.47, 2.48, 2.49, 2.5, 2.51, 2.52, 2.53, 2.54, 2.55, 2.56, 2.57, 2.58, 2.59, 2.6, 2.61, 2.62, 2.63, 2.64, 2.65, 2.66, 2.67, 2.68, 2.69, 2.7, 2.71, 2.72, 2.73, 2.74, 2.75, 2.76, 2.77, 2.78, 2.79, 2.8, 2.81, 2.82, 2.83, 2.84, 2.85, 2.86, 2.87, 2.88, 2.89, 2.9, 2.91, 2.92, 2.93, 2.94, 2.95, 2.96, 2.97, 2.98, 2.99, 3, 3.01, 3.02, 3.03, 3.04, 3.05, 3.06, 3.07, 3.08, 3.09, 3.1, 3.11, 3.12, 3.13, 3.14, 3.15, 3.16, 3.17, 3.18, 3.19, 3.2, 3.21, 3.22, 3.23, 3.24, 3.25, 3.26, 3.27, 3.28, 3.29, 3.3, 3.31, 3.32, 3.33, 3.34, 3.35, 3.36, 3.37, 3.38, 3.39, 3.4, 3.41, 3.42, 3.43, 3.44, 3.45, 3.46, 3.47, 3.48, 3.49, or 3.5 μm.

In the present disclosure, the density of microparticles per fibril may be adjusted and/or varied by altering the mass ratio of starting materials in the steps (a) and (c). According to some embodiments of the present disclosure, the first polymer (i.e., the material for forming the plurality of microparticles) and the second polymer (i.e., the material for forming the first and second fibrils) are respectively present in a mass ratio of about 1:5 to 1:15; for example, about 1:5, 1:6, 1:7, 1:8, 1:9, 1:10, 1:11, 1:12, 1:13, 1:14, or 1:15. In one working example, the mass ratio of the first polymer and the second polymer is about 1:5; in another working example, the mass ratio of the first polymer and the second polymer is about 1:10; in still another working example, the mass ratio is about 1:15.

The first polymer and the second polymer may be same or different materials. In some embodiments, the first polymer and the second polymer are different materials. Examples of the first polymer and second polymer suitable for use in the present method respectively include, but are not limited to, polyurethanes, polysiloxanes, polyethylene, poly(vinyl pyrrolidone), poly(2-hydroxyethyl methacrylate), poly(methyl methacrylate), poly(vinyl alcohol) (PVA), polyacrylic acid, polyacrylamide, poly(ethylene-co-vinyl acetate), poly(ethylene glycol), poly(methacrylic acid), polylactic acid (PLA), polyglycolic acids (PGA), poly(lactic-co-glycolic acid) (PLGA), nylons, polyamides, polyanhydrides, poly(ethylene-co-vinyl alcohol) (EVOH), polycaprolactone (PCL), poly(vinyl acetate), poly(vinyl hydroxide), poly(ethylene oxide) (PEO), polyorthoesters, and a combination thereof. In one working example, the first polymer is PLGA, and the second polymer is PVA.

Optionally or additionally, the present method may further include the step of forming the electrospun fibrous matrix in the presence of a cross-linking agent after the electrospinning step (i.e., the step (d)) to strengthen the structure of the matrix. Any cross-linking agent known to one of ordinary skill in the art may be used in the present method. Examples of the cross-linking agent include, but are not limited to, diisocyanate, methylated melamine formaldehyde resin, N,N-disuccinimidyl suberate, epichlorohydrin, genipin, hexamethylene 1,6-di(aminocarboxysulfonate), glutaraldehyde (GA), and a combination thereof.

Finally, the thus produced fibrils are woven together to form an intact fibrous matrix (i.e., the step (e)). For this purpose, the plurality of first fibrils and second fibrils once being spun out in the solution (e.g., methanol), are weaving and stacking onto each other, thereby forming a woven structure characterized in possessing multiple internal cavities and drug-encapsulating microparticles. In some optional embodiments, the present method further includes removing the solution and curing the woven structure under a room temperature and/or subjected to freeze drying in accordance with the practical needs.

According to embodiments of the present disclosure, the thus produced electrospun fibrous matrix is substantially composed of the plurality of first and second fibrils that are woven together, in which a plurality of cavities are formed therebetween. According to embodiments of the present disclosure, each of the cavities formed in the present electrospun fibrous matrix is about 15-40 μm in diameter. In preferred embodiments, each of the cavities formed in the present electrospun fibrous matrix is about 20-29 μm in diameter.

2.2 Methods for Treating Wounds

The present disclosure also aims at providing treatment to a subject afflicted with unhealed wounds. To this purpose, the present electrospun fibrous matrix may be applied to the wounds and serves as a bio-scaffold and/or drug delivery matrix to help growth of local cells and to treat the wound by the encapsulated drug released therefrom. The present disclosure thus encompasses a method for treating a subject afflicted with a wound.

In some embodiments, the method comprises applying the present electrospun fibrous matrix or that produced by the present method described above to the wounds of the subject. In such embodiments, drugs initially encapsulated in microparticles that integrated within the electrospun fibrous matrix are slowly released to the lesion, thereby accelerating wound healing process.

According to embodiments of the present disclosure, the drug can be an analgesic agent, an anti-inflammatory agent, an anti-cancer agent, an antibiotic, or a combination thereof, as described in Section 2.1 of this paper. In some preferred embodiments, the drug encapsulated in the microparticle is dexamethasone, celecoxib, paclitaxel, nobiletin, or tangeretin. To treat a wound, any clinical artisans may choose a suitable agent for use in the present method based on factors such as the particular condition being treated, the severity of the condition, the individual patient parameters (including age, physical condition, size, gender and weight), the duration of the treatment, the nature of concurrent therapy (if any), and like factors within the knowledge and expertise of the health practitioner.

According to some optional embodiments of the present disclosure, the present method further comprises administering to the subject an effective amount of isolated stem cells, isolated somatic cells, or a combination thereof. In such embodiments, external cells (i.e., isolated cells) accompanied by the present electrospun fibrous matrix are administered to the wounds of the subject, and the cavities of the matrix provide suitable spaces for cell adhesion and growth, so as to improve the efficiency of tissue repairing.

Examples of stem cells suitable for use in the present method include, but are not limited to, mesenchymal stem cells, adult stem cells, embryonic stem cells, bone marrow stem cells, neural stem cells, limbal stem cells, tissue-derived stem cells, dental pulp stem cells, and induced pluripotent stem cells. In one working example, the isolated stem cells are dental pulp stem cells.

Examples of somatic cells suitable for use in the present method include, but are not limited to, muscle cells, hepatocytes, neurons, fibroblasts, odontoblasts, epithelial cells, adipocytes, bone cells, leukocytes, lymphocytes, platelets, and mucosal cells. In one working example, the isolated somatic cells are fibroblasts; in another working example, the isolated somatic cells are macrophages.

According to some embodiments of the present disclosure, the isolated stem cells or the isolated somatic cells are administered to the subject having wounds in an amount sufficient to accelerating wound healing and tissue regeneration. According to some embodiments of the present disclosure, the isolated stem cells or the isolated somatic cells are administered to the subject in the amount of about $1 \times 10^4$ to $1 \times 10^6$ cells per square centimeter of the wound area of the subject; for example, about $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, or $1 \times 10^6$ cells per square centimeter of the wound area. In one specific example of the present disclosure, the isolated cells are administered in the amount of about $2 \times 10^4$ cells/cm$^2$ The present isolated stem cells and/or the isolated somatic cells can be administered at a frequency that effectively helps and accelerates the wound healing. In some embodiments, the isolated cells can be administered at a frequency of four times a day to once every three months; for example, at a frequency of four times a day, three times a day, twice a day, once a day, once every other day, once every third day, once every week, once every other week, once monthly, once every other month, or once every three months. Preferably, the isolated cells are administered to the subject at a frequency of once every fourteen days (two weeks).

By the virtue of the above features, the present method can provide bio-scaffolds that do not only possess three-dimension structure for cell regeneration, but also serve as a drug-delivery vehicle for releasing drugs to the lesions, thereby allowing the wounds to be rapidly and efficiently healed.

EXAMPLES

Materials and Methods

Electrospun Fibrous Matrix Preparation

Stage I Encapsulation of Dexamethasone within Poly(Lactic-Co-Glycolic Acid)

Poly(lactic-co-glycolic acid) (PLGA) (100 mg dissolved in 5 ml dichloromethane (DCM)) and dexamethasone (25 mg dissolved in 1.5 ml ethanol) were mixed to form a mixture in ice bath and sonicating the mixture for 2 mins (130 W, 60%). After sonication, 10 ml of 1% polylactic acid (PLA) was added into the mixed solution, which was stirred with a magnetic stirrer (240 rpm) with a constant suction (i.e., negative pressure) at 40° C. for 15 to 20 minutes. The mixture was centrifuged by 10,000 rpm at 4° C. for 10 minutes, and the precipitated solids were collected and redissolved with ddH$_2$O, such that the microparticles made of PLGA and having dexamethasone encapsulated therein were obtained.

Stage II Wet Electrospinning Process

The thus produced microparticles in Stage I were mixed with 5 ml PVA dissolved in ddH$_2$O and subjected to constant stirring for 8 hours. The mixture was then passed to a syringe pump for a wet electrospinning process, which was driven by the voltage of 16 kV to 22 kV at flow rate of 0.6 to 1 mL/hour to the droplets of the mixture. The spinning process lasted for 5 hours at an environmental humidity of about 22-55%, and the thus-produced fibrils were woven together to generate a woven structure, which was immersed in a methanol solution until the PVA-made fibrils were fully collected. The woven structure was then cured at room temperature for 4 hours, and lyophilized overnight at −80° C. to give the desired electrospun fibrous matrix.

Porosity of Electrospun Fibrous Matrix

The porosity of the present electrospun fibrous matrix was analyzed using visual descriptor software to estimate the Feret dimeter (F) of each cavity identified from microscopic photos. The Feret dimeter (F) was calculated according to the formula:

$$F = \frac{P}{\pi}$$

where P represents the perimeter of a cavity.

Drug Release Kinetics Test

The present electrospun fibrous matrices were placed in phosphate buffered saline (PBS) respectively at different temperature of 4° C. and 37° C., and the amount of releasing drug (i.e., dexamethasone) was recorded at each time point of 0.25, 0.5, 1, 3, 6, 12, 24, 48, 72, 96, 120, 144, and 168 hours later.

Biodegradability Test

Each electrospun fibrous matrix was immersed into PBS solution at 25° C. or 37° C., respectively. The electrospun fibrous matrix was taken out from the solution to the oven-dry at 40° C. and weighed once every day for at least fifteen days.

Cell Lines and Cultivation Conditions

Human diploid fibroblasts (IMR-90), dental pulp stem cells (DPSCs), and the mouse macrophage line RAW264.7 were obtained from American Type Culture Collection (ATCC). Fibroblasts and dental pulp stem cells were cultured in MEM-α with 10% FBS in a cell culture chamber at 37° C. in a humidified atmosphere with 5% $CO_2$; while RAW 264.7 macrophages were cultured in DMEM medium supplemented with 5% FBS, 100 U/ml penicillin and 100 μg/ml streptomycin and placed in the cell culture chamber as the same humidity and temperature condition.

Cell Viability Test and Cell Number Measurement

Three types of electrospun fibrous matrices: (1) an electrospun fibrous matrix produced in method set forth above in Stage I and II, referred by the term of "PLGA-PVA matrix" hereinafter; (2) an electrospun matrix produced only by wet electrospinning process described in Stage II (i.e., without drug-containing microparticles, referred by the term of "PVA matrix without PLGA" hereinafter; and (3) a comparative matrix produced by a dry electrospinning process, referred to as "conventional PVA matrix" hereinafter, were respectively co-cultivated with dental pulp stem cells in a 96-well plate by inoculating $2 \times 10^4$ cells per well.

In addition, IMR-90 and RAW264.7 cells were further cultivated in 96-well plates by individually inoculating $2.5 \times 10^3$ cells per well in the existence or absence of the present PLGA-PVA matrix (thickness 1.5 mm×diameter 6 mm). The wells absence of the present PLGA-PVA matrix served as a control group.

To measure the cell number, cells were suspended in a 96-well plate and pre-incubated at 37° C. in a humidified chamber with 5% $CO_2$. 10 μl of the Cell Counting Kit-8 (CCK-8) solution (TEN-CCK81, Tools-biotech) was added into each well of the plate, followed by further incubation for 2 hours. The absorbance at 450 nm of each well was measured by microplate reader (HBS-1096A, DeTie) and recorded at different time points.

Example 1 Characterization of the Present Electrospun Fibrous Matrix

Figure 1B:
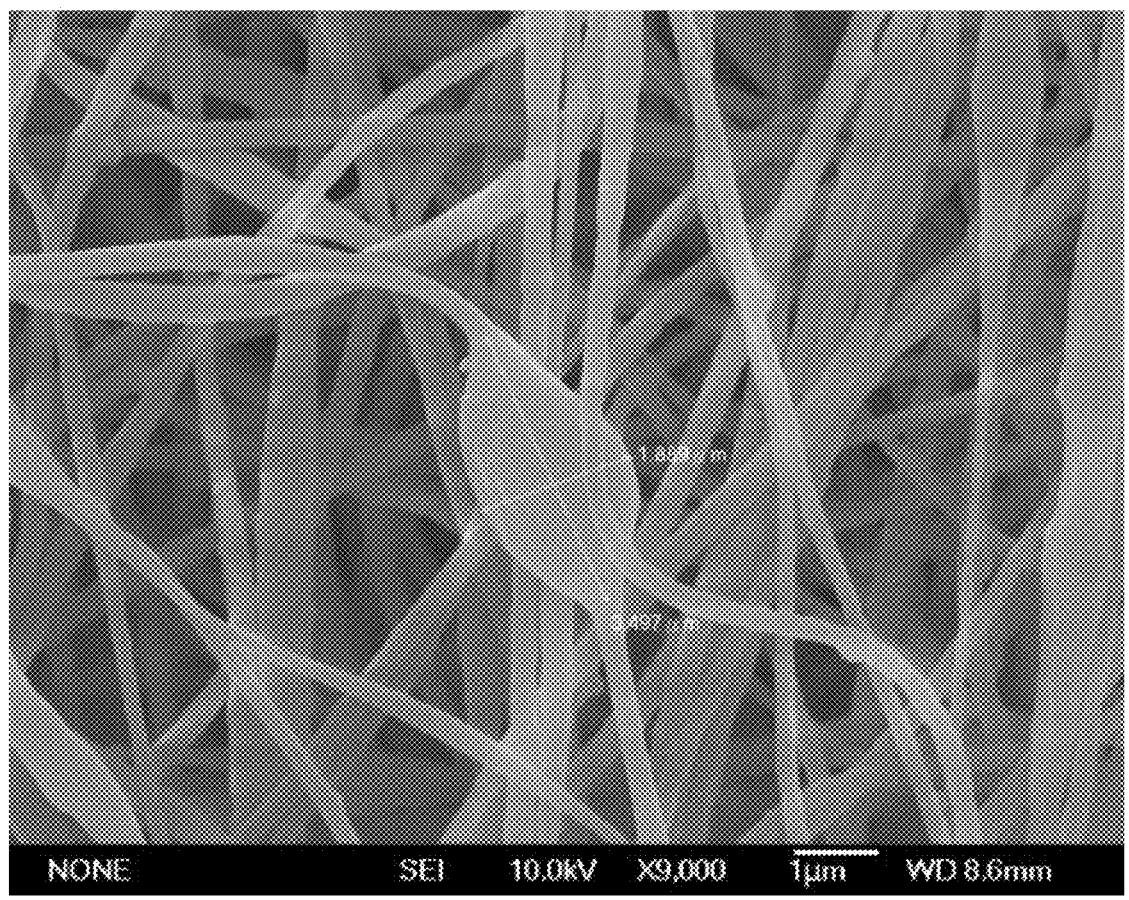

The present electrospun fibrous matrix was produced by the method described in the "Materials and Methods" section. In this example, the morphology of the electrospun fibrous matrix was examined by electron microscopy, and results are shown in FIGS. 1A and 1B. It was evident from the photograph of FIG. 1A that the electrospun fibrous matrix was constituted by two types of fibrils woven together, which included a bare fibril, and a fibril integrated with a plurality of microparticles independently disposed along the longitudinal direction thereof, resembling a string of beads. The photograph of FIG. 1B revealed the detail structure of a microparticle in FIG. 1A. It is evident from the magnified photo of FIG. 1B that the microparticle had a diameter larger than that of the fibril.

Figure 2:
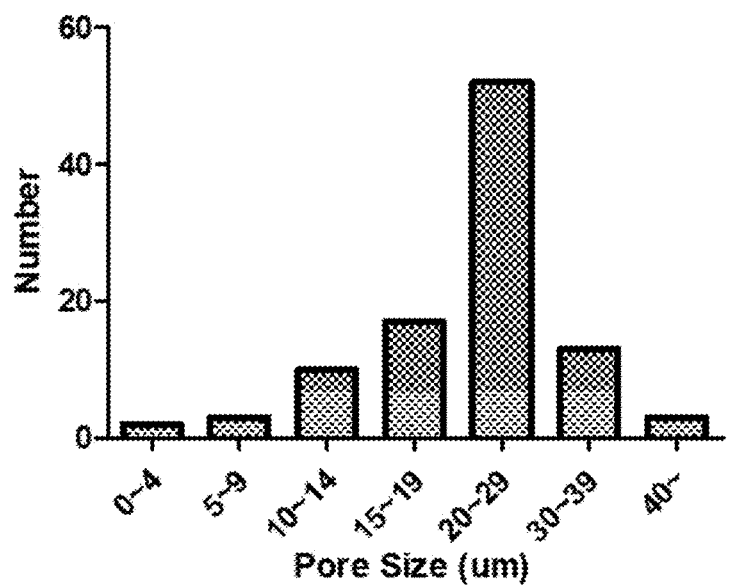
FIG. 2 is a bar graph depicting the size of cavities in the electrospun fibrous matrix estimated by electron microscope according to one embodiment of the present disclosure.

The porosity of the present electrospun fibrous matrix was estimated by examining the Feret dimeter (F) of each cavity identified from the photograph of FIG. 1A. Results are illustrated in FIG. 2. As depicted in FIG. 2, most of the cavities were independently about 20 to 29 μm in diameter, and the average diameter was larger than that of a conventional spinning matrix (data not shown).

Figure 3:
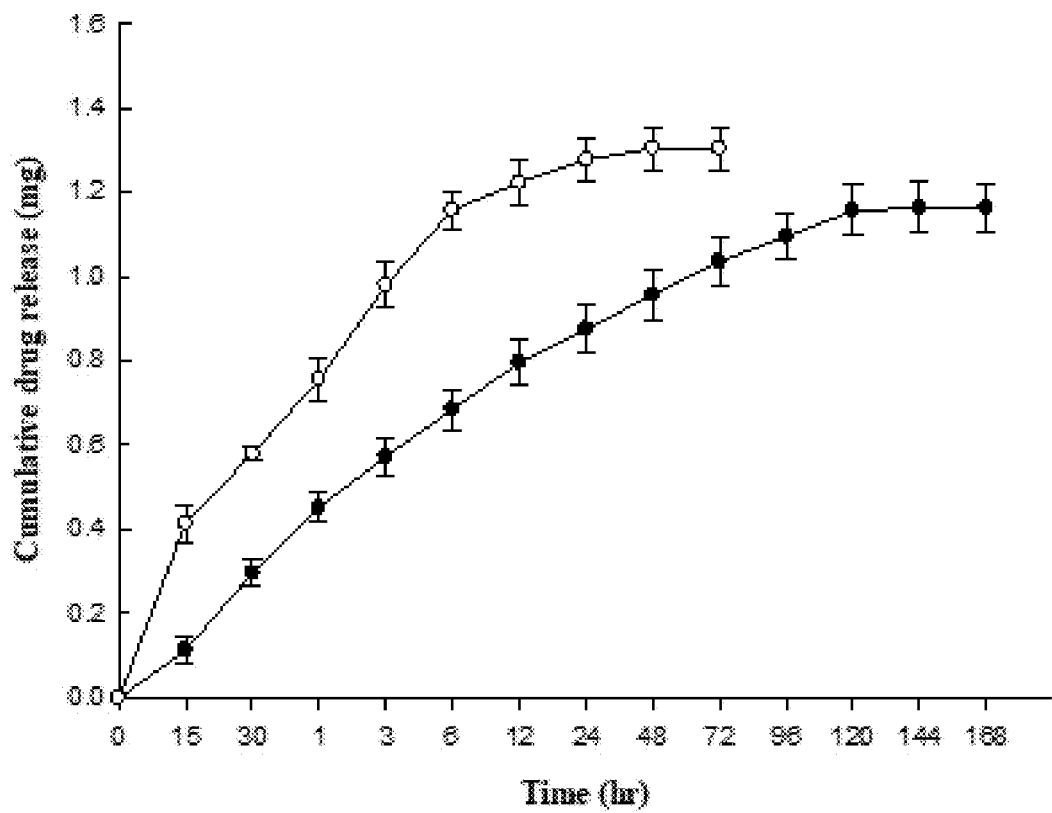
FIG. 3 depicts the drug release efficiency of the present electrospun fibrous matrix in accordance with one embodiment of the present disclosure.
Figure 4:
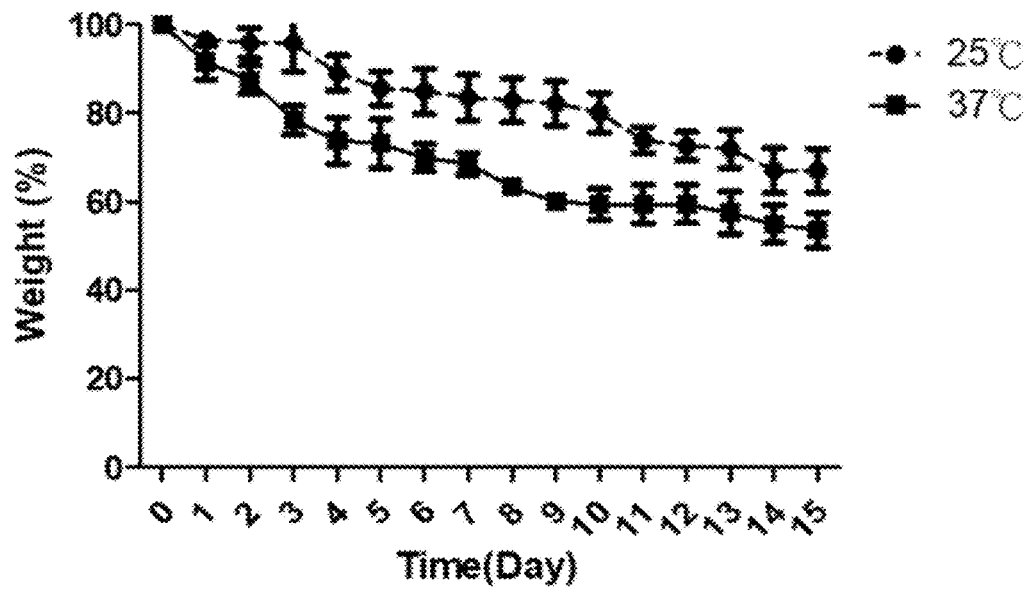
FIG. 4 depicts the biodegradability of the electrospun fibrous matrix according to one embodiment of the present disclosure.
Figure 5:
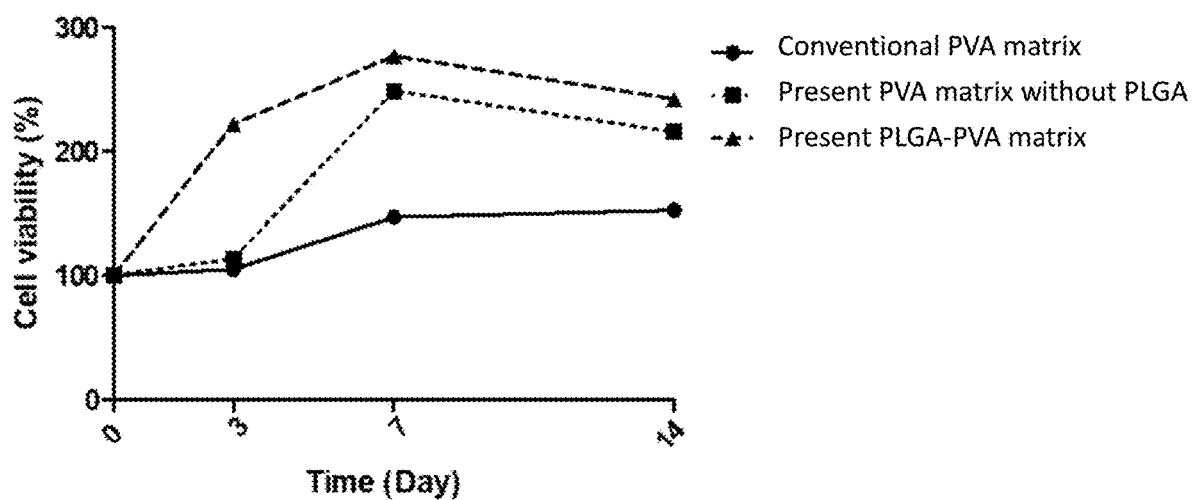
FIG. 5 depicts the cell viability of dental pulp stem cells grew on the present electrospun fibrous matrices in accordance with one embodiment of the present disclosure.

Example 2 Effects of the Present Electrospun Fibrous Matrix on Wound Healing In this example, the effect of the present electrospun fibrous matrix on wound healing was investigated by factors including drug release kinetics, biodegradability, and cell viability in accordance with procedures described in the "Materials and Methods" section, and results are provided in FIGS. 3 to 5.

FIG. 3 depicts the drug release kinetic of the present electrospun fibrous matrices. It was found that after 72 hours, the cumulative dexamethasone released from the present electrospun fibrous matrices was about 1.1 mg/ml at 4° C., and 1.3 mg/ml at 37° C., suggesting that the present electrospun fibrous matrices had a better drug release kinetic at human body temperature.

FIG. 4 depicts the biodegradability of the present electrospun fibrous matrices. It was found that after fifteen days, the degradation weight loss of the present electrospun fibrous matrix was about 30% at 25° C. and 50% at 37° C., suggesting that the present electrospun fibrous matrix was biodegradable and biocompatible, particularly at human body temperature.

FIG. 5 depicts the viabilities of dental pulp stem cells grew on various electrospun fibrous matrices as described in the "Materials and Methods" section. Compared to the conventional PVA matrix, both the present matrices (i.e., the PLGA-PVA matrix and the PVA matrix without PLGA) greatly improved the cell viability of dental pulp stem cells. Specifically, it was found that the maximum viability of dental pulp stem cells reached to 277% of the initial cell number in the existence of the present PLGA-PVA matrix at day 7, but only reached to 103% when co-cultivated with the conventional PVA matrix, suggesting that the present electrospun fibrous matrix provided a better cell growth efficiency over the comparative matrix because of its intact structure and ideal porosity.

Further, it was observed that the dental pulp stem cells all filled into the cavities of the present PLGA-PVA matrix under confocal microscopy (data not shown), suggesting that the present electrospun fibrous matrix provided a superior three-dimensional environment for cell growth in the wounds, particularly for deep wounds in dental pulps.

Example 3 Versatility of the Present Electrospun Fibrous Matrix as Bioscaffolds In this example, whether the present electrospun fibrous matrix versatile enough for various types of cells to grow thereon was investigated by examining cell viability of two cell lines other than dental pulp stem cells in accordance with the protocol described in the "Materials and Methods" section, and results are provided in FIGS. 6A to 7B.

Figure 6A:
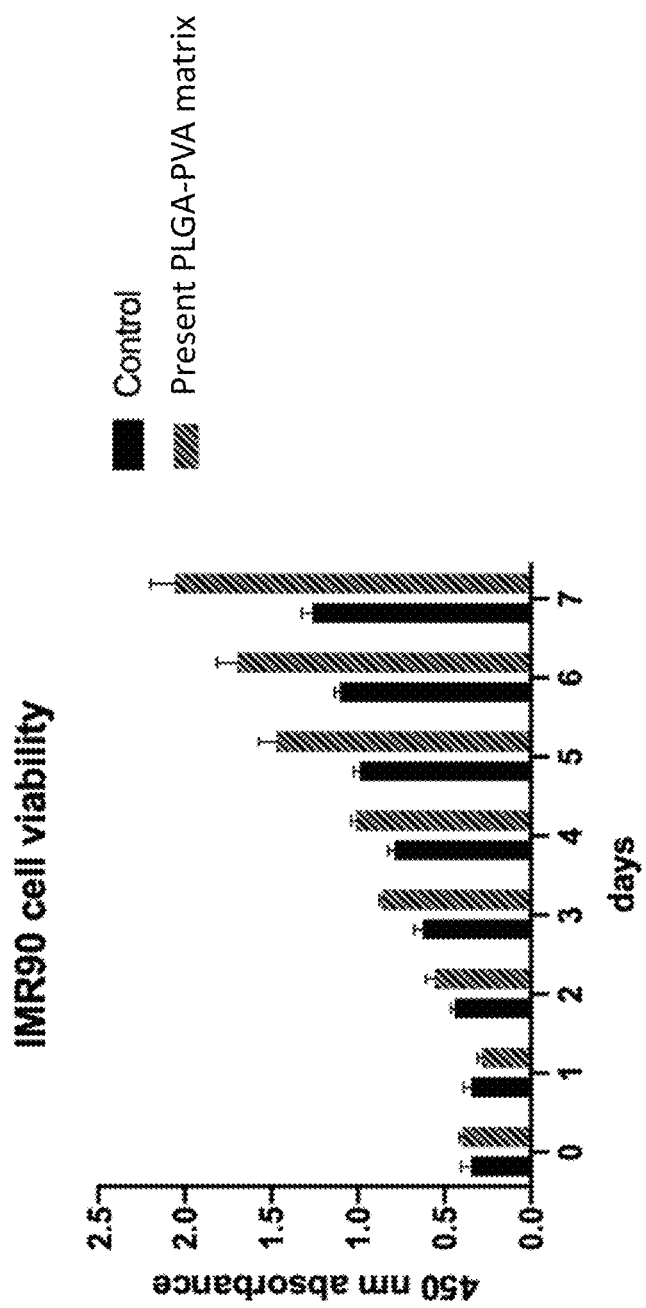
FIG. 6A are bar graphs depicting cell viability of fibroblasts IMR-90 in the presence of the present PLGA-PVA matrix in accordance with another embodiment of the present disclosure.
Figure 6B:
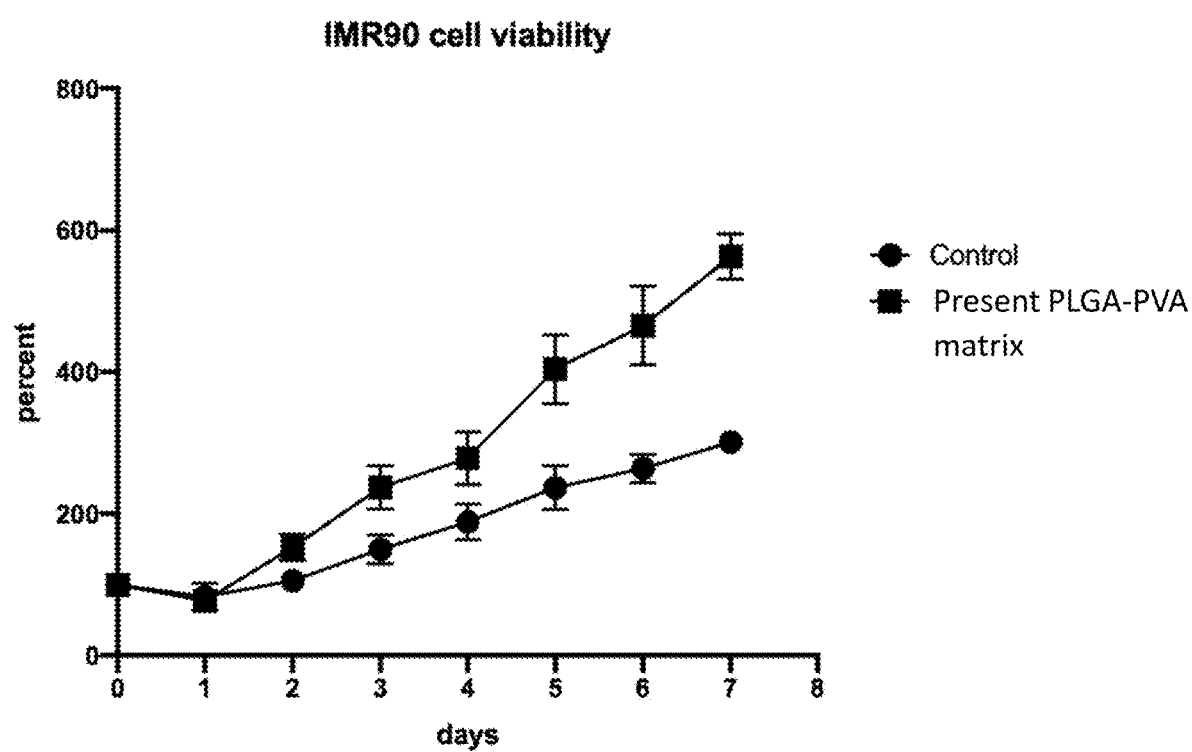
FIG. 6B are line graphs depicting cell viability of fibroblasts IMR-90 in the presence of the present PLGA-PVA matrix in accordance with another embodiment of the present disclosure.

References are made to FIGS. 6A and 6B, in which it was found that, compared to the control group, the cell viability of fibroblasts significantly increased from day 2 after being inoculated into the present electrospun fibrous matrix. Specifically, the number of IMR-90 cells reached to the maximum level (i.e., 577% of the initial cell number) in the presence of the present PLGA-PVA matrix at day 7, and was about two-folds of the control group, in which the PLGA-PVA matrix was absent.

Figure 7A:
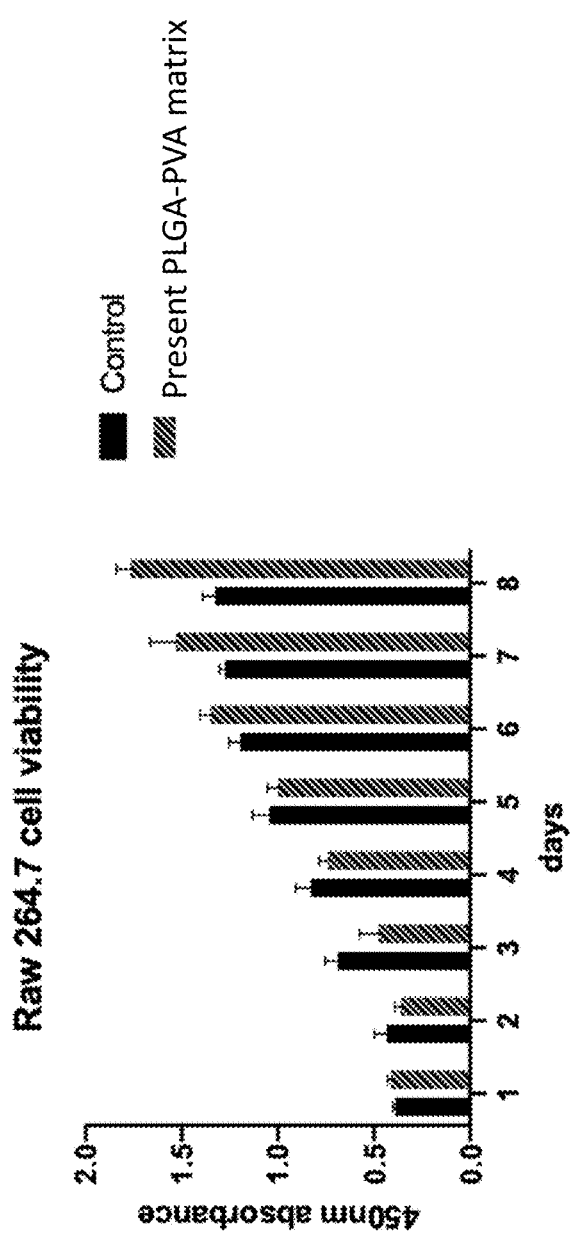
FIG. 7A are bar graphs depicting cell viability of macrophages RAW 264.7 in the presence of the present PLGA-PVA matrix in accordance with another embodiment of the present disclosure.
Figure 7B:
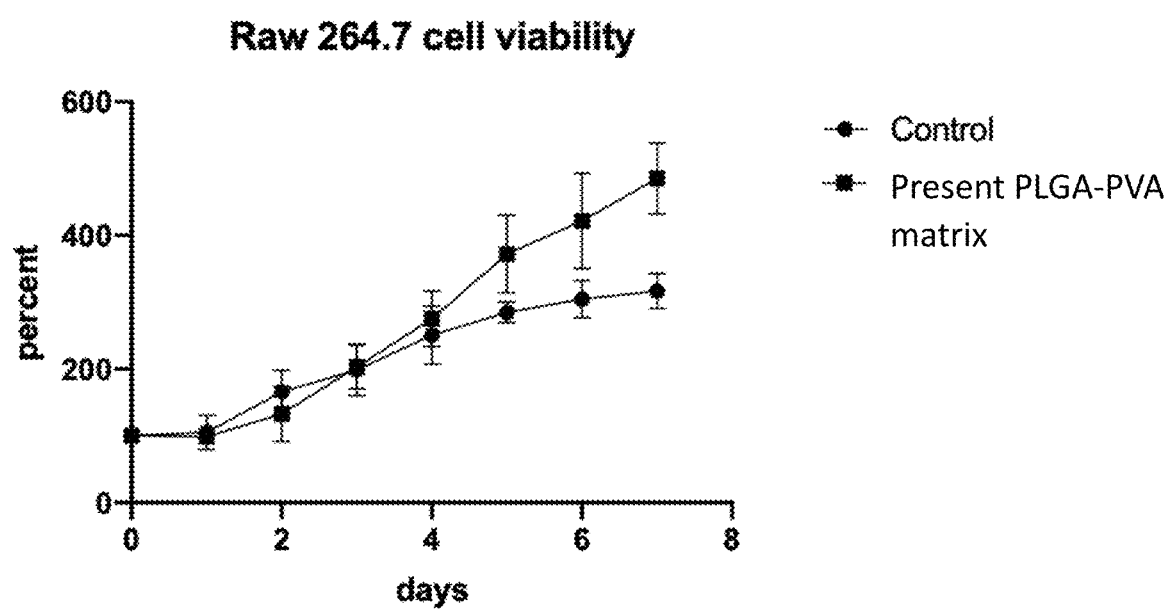
FIG. 7B are line graphs depicting cell viability of macrophages RAW 264.7 in the presence of the present PLGA-PVA matrix in accordance with another embodiment of the present disclosure.

Similar results were also observed in the viability of macrophages RAW 264.7 grew on the present PLGA-PVA matrix (FIGS. 7A and 7B). It was found that the macrophages RAW 264.7 co-cultivated with the present PLGA-PVA matrix exhibited a greater cell viability compared to those cultivated in control plates without the presence of PLGA-PVA matrix, specifically on day $4^{th}$ after inoculation. In the presence of the present PLGA-PVA matrix, the maximum number of RAW 264.7 reached to a maximum level that was about 485% of the initial cell number, while the number of RAW 264.7 in the control group reached to a level of about 300%.

Taken together, the data depicted in FIGS. 6 and 7 collectively indicates that the present electrospun fibrous matrix are versatile for various cell lines including fibroblasts, macrophages, and the like to grow thereon.

In conclusion, the present disclosure provides an improved electrospun fibrous matrix that possesses integrated drug-encapsulated microparticles as a drug delivery panel and a high porosity that allows cells to efficiently grow thereon, thereby accelerating the wound healing. Further, the present electrospun fibrous matrix is versatile for different cells to grow thereon, allowing a more extensive application for repair of various tissues.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An electrospun fibrous matrix, comprising a plurality of a first and second fibrils that are woven together, wherein,
    each of the second fibrils has a plurality of microparticles independently integrated within the second fibril and disposed at intervals along the longitudinal direction of each of the second fibrils, wherein each of the microparticles is made of a first polymer and has a encapsulated therein,
    each of the first fibrils is devoid of the microparticles and the drug; and
    the plurality of the first and second fibrils are independently made of a second polymer that is different from the first polymer wherein the first polymer is poly(lactic-co-glycolic acid) (PLGA) and the second polymer is poly(vinyl alcohol) (PVA).

2. The electrospun fibrous matrix of claim 1, wherein each of the first fibrils has a diameter ranging from 100 to 500 nm, and each of the microparticles is about 1 to 5 µm in diameter.

3. The electrospun fibrous matrix of claim 1, wherein the electrospun fibrous matrix has a plurality of cavities independently being about 15-40 µm in diameter.

4. The electrospun fibrous matrix of claim 1, wherein the drug is an analgesic agent, an anti-inflammatory agent, an anti-cancer agent, an antibiotic, or a combination thereof.

5. A method of producing an electrospun fibrous matrix, comprising:
    (a) mixing a first polymer and a drug to form a first mixture;
    (b) sonicating the first mixture of the step (a) until a plurality of microparticles are formed with the drug being encapsulated therein;
    (c) mixing the plurality of microparticles of the step (b) with a second polymer to form a second mixture;
    (d) subjecting the second mixture of the step (c) to an electrospinning process in a solution to produce a plurality of first and second fibrils, wherein each of the second fibrils has the plurality of microparticles independently integrated and disposed along the longitudinal direction of the second fibrils, while each of the first fibrils is devoid of the microparticles; and
    (e) weaving the plurality of first and second fibrils to form the electrospun fibrous matrix,
    wherein the first polymer and the second polymer are different wherein the first polymer is poly(lactic-co-glycolic acid) (PLGA) and the second polymer is poly(vinyl alcohol) (PVA).

6. The method of claim 5, wherein in the step (a), the first polymer and the drug are mixed at a mass ratio about 5:1 to 3:1.

7. The method of claim 5, wherein the first polymer and the second polymer exist in a mass ratio of about 1:5 to 1:15.

8. The method of claim 5, wherein the drug is an analgesic agent, an anti-inflammatory agent, an anti-cancer agent, an antibiotic, or a combination thereof.

9. The method of claim 5, wherein in the step (d), the electrospinning process is conducted under a humidity of about 20-55% at a voltage of about 16-22 kV for about 5 hours.

10. The method of claim 5, wherein in the step (d), the solution is a methanol solution.

11. A method for treating a wound in a subject in need thereof, comprising applying the electrospun fibrous matrix of claim 1 to the wound of the subject.

12. The method of claim 11, further comprising administering to the subject an effective amount of isolated stem cells, isolated somatic cells, or a combination thereof.

13. The method of claim 12, wherein the isolated stem cells are selected from the group consisting of mesenchymal stem cells, adult stem cells, embryonic stem cells, bone marrow stem cells, neural stem cells, limbal stem cells, tissue-derived stem cells, dental pulp stem cells, and induced pluripotent stem cells.

14. The method of claim 12, wherein the isolated somatic cells are selected from the group consisting of muscle cells, hepatocytes, neurons, fibroblasts, odontoblasts, epithelial cells, adipocytes, bone cells, leukocytes, lymphocytes, platelets, and mucosal cells.

15. The method of claim 12, wherein the isolated stem cells or the isolated somatic cells are administered to the subject in the amount of about $1 \times 10^4$ to $1 \times 10^6$ cells per square centimeter of a wound area.

* * * * *